United States Patent
Xue et al.

(10) Patent No.: US 7,813,792 B2
(45) Date of Patent: Oct. 12, 2010

(54) METHOD AND APPARATUS FOR ANALYZING AND EDITING ECG MORPHOLOGY AND TIME SERIES

(75) Inventors: Joel Q. Xue, Germantown, WI (US); Paul P. Elko, River Hills, WI (US)

(73) Assignee: General Electric Company, Schenectady, NY (US)

( * ) Notice: Subject to any disclaimer, the term of this patent is extended or adjusted under 35 U.S.C. 154(b) by 936 days.

(21) Appl. No.: 11/405,150

(22) Filed: Apr. 17, 2006

(65) Prior Publication Data

US 2007/0244401 A1    Oct. 18, 2007

(51) Int. Cl.
A61B 5/044    (2006.01)
A61B 5/0464   (2006.01)
A61B 5/046    (2006.01)

(52) U.S. Cl. .......................... 600/523; 607/30; 607/59
(58) Field of Classification Search .................. 600/523; 607/30, 59

See application file for complete search history.

(56) References Cited

U.S. PATENT DOCUMENTS

| | | | |
|---|---|---|---|
| 5,277,189 A | 1/1994 | Jacobs | |
| 5,325,856 A | 7/1994 | Nitzsche et al. | |
| 6,324,423 B1 | 11/2001 | Callahan et al. | |
| 6,438,409 B1 * | 8/2002 | Malik et al. | 600/512 |
| 2002/0165459 A1 | 11/2002 | Starobin et al. | |
| 2003/0130586 A1 * | 7/2003 | Starobin et al. | 600/515 |
| 2005/0010124 A1 * | 1/2005 | Couderc et al. | 600/515 |

FOREIGN PATENT DOCUMENTS

| | | |
|---|---|---|
| EP | 1 190 672 A2 | 3/2002 |
| EP | 1 529 487 A1 | 5/2005 |

OTHER PUBLICATIONS

Appendix A—ECG Interval Editor Option—30 pages.
QT Analysis Tool—pp. 1-2.
GB Search Report dated Aug. 13, 2007.
Translated Chinese Office Action issued Nov. 27, 2009.

* cited by examiner

*Primary Examiner*—Carl H. Layno
*Assistant Examiner*—Tammie K Heller
(74) *Attorney, Agent, or Firm*—Andrus, Sceales, Starke & Sawall, LLP

(57) ABSTRACT

A method and apparatus for analyzing the QT interval characteristics of ECG signal data having a succession of waveforms produced by the beating of the heart. ECG signal data is obtained from a patient. The R-R interval and the QT intervals of the waveforms of the ECG signal data are determined. Waveforms of the ECG signal data having a stable heart rate are selected for use in determining the QT interval characteristics. Preferably, the waveforms selected are those having minimum R-R interval standard deviation and minimum R-R interval dispersion. The QT correction (QTc) is computed from the ECG signal data waveforms selected in the foregoing manner or on the basis of clinician editing. The R-R intervals, the QT intervals, and QTc for the heart beats of the selected waveforms are displayed for analysis and diagnosis purposes. The invention can also be used, in an analogous manner, to obtain and display other cardiac data from the ECG waveforms.

19 Claims, 8 Drawing Sheets

DEPOLARIZATION

HEART RATE
R-R INTERVAL
QRS AXIS
QRS AMPLITUDE
Q DURATION

REPOLARIZATION

Q-T INTERVAL
T AXIS
Q-T DISPERSION
T AMPLITUDE

VENTRICULAR
DEPOLARIZATION

R-R INTERVAL
QRS AXIS
QRS AMPLITUDE
Q DURATION

ATRIAL
DEPOLARIZATION

P-R INTERVAL
P AXIS
P-R DISPERSION
P WAVE DURATION

METHOD AND APPARATUS FOR ANALYZING AND EDITING ECG MORPHOLOGY AND TIME SERIES

BACKGROUND AND SUMMARY

The present invention relates to a method and apparatus for analyzing and editing the morphology and time series relationships in electrocardiographic (ECG) signals.

The heart has a right side that circulates blood to the lungs for oxygenation and $CO_2$ discharge and a left side that circulates oxygenated blood to the systemic circulatory vascular field of the body. Each side has an atrium that receives blood during relaxation of the heart muscle (diastole) and a ventricle that discharges blood when the heart muscle contracts (systole).

ECG signal data reflects the electrical activity of the heart conduction system and muscle in pumping blood through the lungs and systemic circulatory field of a subject. The signal contains a succession of waveforms produced by the repetitive action, or beating, of the heart. For a normal heart rate of about 60 to 80 beats per minute, the waveforms are produced about every 0.75 to 1 second or about every 750 to 1000 milliseconds.

A typical ECG waveform is shown in FIG. 1. It comprises a P wave, a QRS complex, and a T wave. The P wave is caused by the electric potentials generated when the atria of the heart depolarize before atrial contraction occurs. The QRS complex is caused by the potentials generated when the ventricles depolarize before their contraction and features the prominent R peak. As the contraction and pumping action of the heart occurs, repolarization of the heat muscle commences, slowly at first and then more rapidly as the ECG waveform concludes in the T wave, in some cases, in a U wave.

In addition to the presence and shape of the components of the ECG waveform (i.e. the morphology), the length of the components, and the spacing, or interval, between the components is useful in ECG interpretation. Commonly used intervals shown in FIG. 1 are the P-R interval, QRS duration, the ST-T segment, and the QT interval. The U wave, which is a slight depression in the S-T segment of the ECG waveform, believed to the attributable to late repolarization of certain parts of the heart may also be used.

The use of certain drugs, or combinations of drugs, can affect the ion channels of cardiac cells and is reflected in changes in the characteristics of ECG waveforms. An example of this is the use of drugs such as some anti-depressants and anti-retrovirals, that induce a prolongation of the QT interval. This prolongation can lead to a life threatening arrhythmia in the form of a ventricular tachycardia (excessive rapidity) termed "torsade de pointes", often referred to simply as "torsade," or TdP. Use of the QT interval is currently the only technique approved by regulatory authorities to predict possible drug induced TdP in clinical drug trials.

For this reason, efforts have been directed to obtaining a proper measurement of the QT interval, as well as accurate computation of a correction of the QT intervals of the ECG waveforms of a time series. This correction, QTc, is used to adjust the determination of the QT interval for changes in the heart rate. Previously, the QT interval was usually corrected based on an immediately previously occurring R-R interval. The R-R interval is the interval between the R peaks of successive waveforms. However, more and more research has shown that there could be some delay effects between R-R interval change and QT interval change. This delay effect, often also called "hysteresis," can be as long as 2 minutes in some cases. But in most practical situations, only a short segment of ECG signal data, for example, 10 seconds of data, is available. It can make a large difference if different ECG beats are selected for the QTc calculation if there is some type of arrhythmia in the heart beat, as evidenced by an irregular R-R interval. Therefore, it is important to select a proper group of ECG beats for the QTc calculation within the available, short segment of ECG signal data.

Currently, in carrying out the measurement of the QT interval and QT correction (QTc), an amount of ECG signal is subjected to analysis using an ECG analysis algorithm to flag those ECG waveforms in the signal deemed suitable for QT interval and QTc measurement. The signal data is then reviewed by a cardiologist or other clinician who decides which waveforms to use for the QT interval measurement and QTc computation. While this selection is designed to improve the quality of data used to compute the QT quantities and improve the ultimate accuracy of the determination, at present, it is often an arduous task for the clinician.

SUMMARY OF THE PRESENT INVENTION

In determining the QT interval and the QTc, the method and apparatus of embodiments of the present invention obtains ECG signal data and determines the R-R intervals and QT intervals for the waveforms in the data. Portions of the ECG signal data exhibiting relatively stable heart rate are selected. The selection of the stable heart rate waveforms may be based on a comparison of the standard deviation for the intervals between the R features of the ECG waveforms, i.e. the R-R interval. The dispersion between the maximum R-R interval and the minimum R-R interval in the waveforms may also be used.

Specifically, the waveforms of ECG signal data selected are those having a minimum standard deviation of the R-R interval and a minimum dispersion of the R-R interval. Manual selection may be aided by a novel display that graphically relates the R-R intervals and the QT intervals of the waveforms. From the selected ECG signal data, the QTc is computed.

Thereafter, the R-R interval, the QT interval, and the QTc are displayed for each selected heart beat of the ECG signal data to allow analysis of the Q-T properties and diagnosis based thereon.

While the ECG signal data has been described as being analyzed for longer QT intervals, as a predictor of TdP, it will be appreciated that the analysis may also be directed to the determination of the presence of abnormally short QT intervals. Short QT intervals have also been linked to life threatening arrhythmias.

More generally, the technique of the present invention may be used to obtain and display data sets comparing two or more cardiac related conditions in a manner useful for diagnostic purposes.

Embodiments of the present invention will be further understood from the following detailed description, taken in conjunction with the drawing.

DETAILED DESCRIPTION

Figure 1:
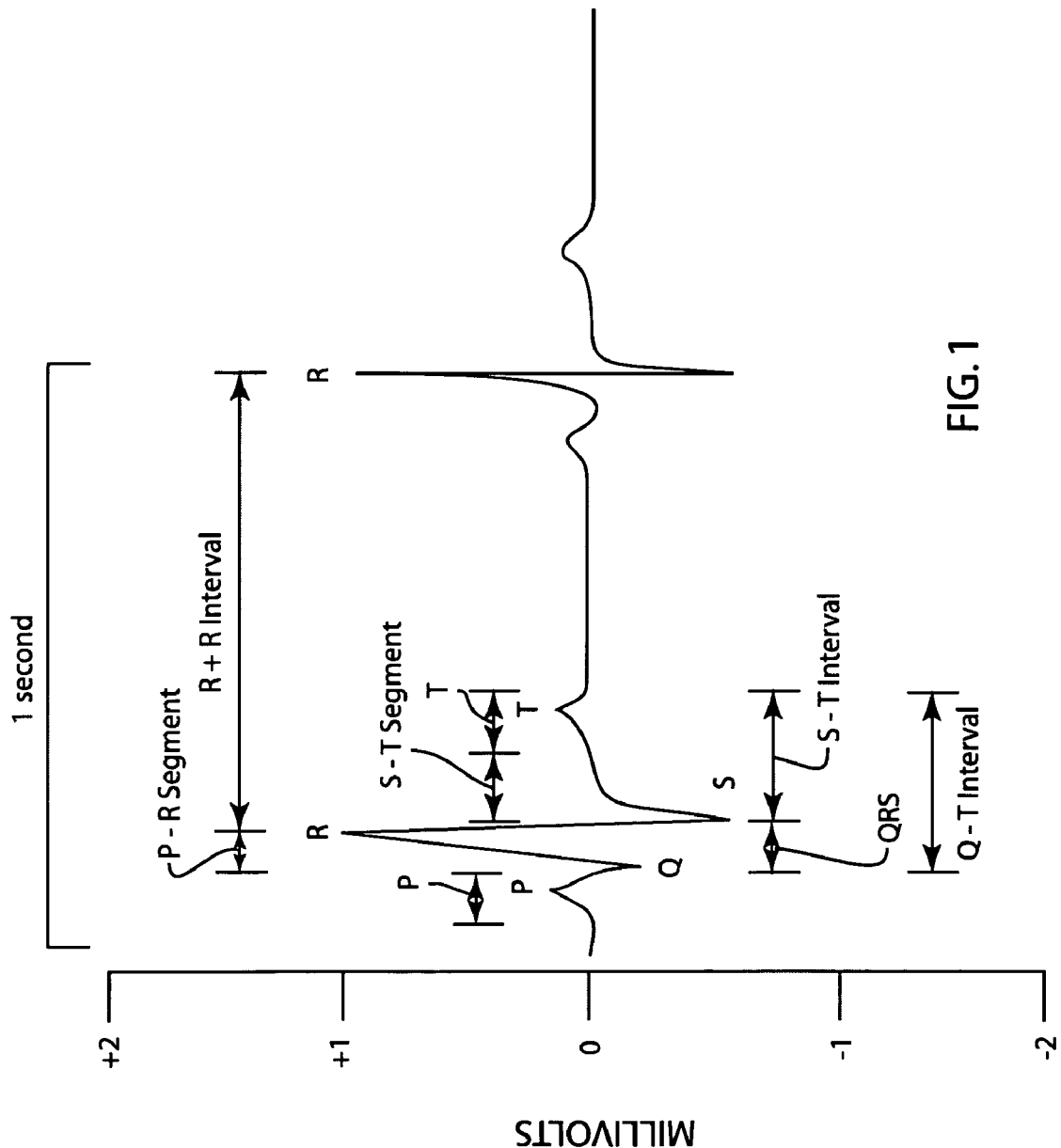
FIG. 1 shows electrocardiographic waveforms.
Figure 2:
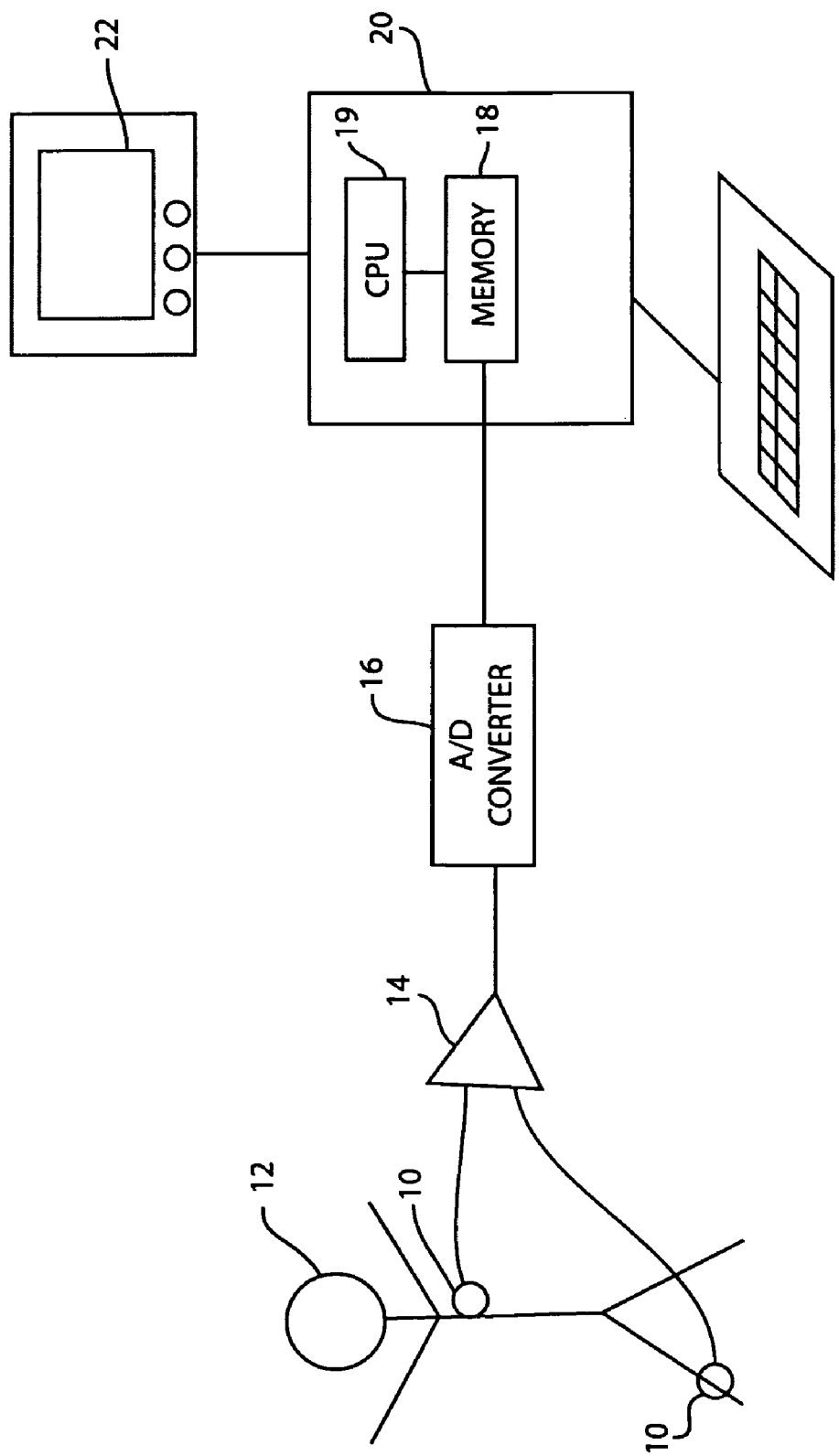
FIG. 2 is a simplified schematic drawing showing an apparatus of the present invention.

For use in the present invention, ECG signal data is obtained in a conventional manner by applying electrodes 10 to the body of a subject 12, as shown in FIG. 2. In the apparatus of the present invention, the electric signals in electrodes 10 are amplified in pre-amplifier 14 and are in the analog form shown in FIG. 1 comprising a series of sequential waveforms. The analog signals are subjected to analog-to-digital conversion in analog/digital converter 16 and stored in the memory 18 of computer 20, the operation of which using central processor unit 19 containing an algorithm that carries out the method of the present invention. Computer 20 includes a screen 22 for displaying information in graphic and/or textual form.

Figure 3:
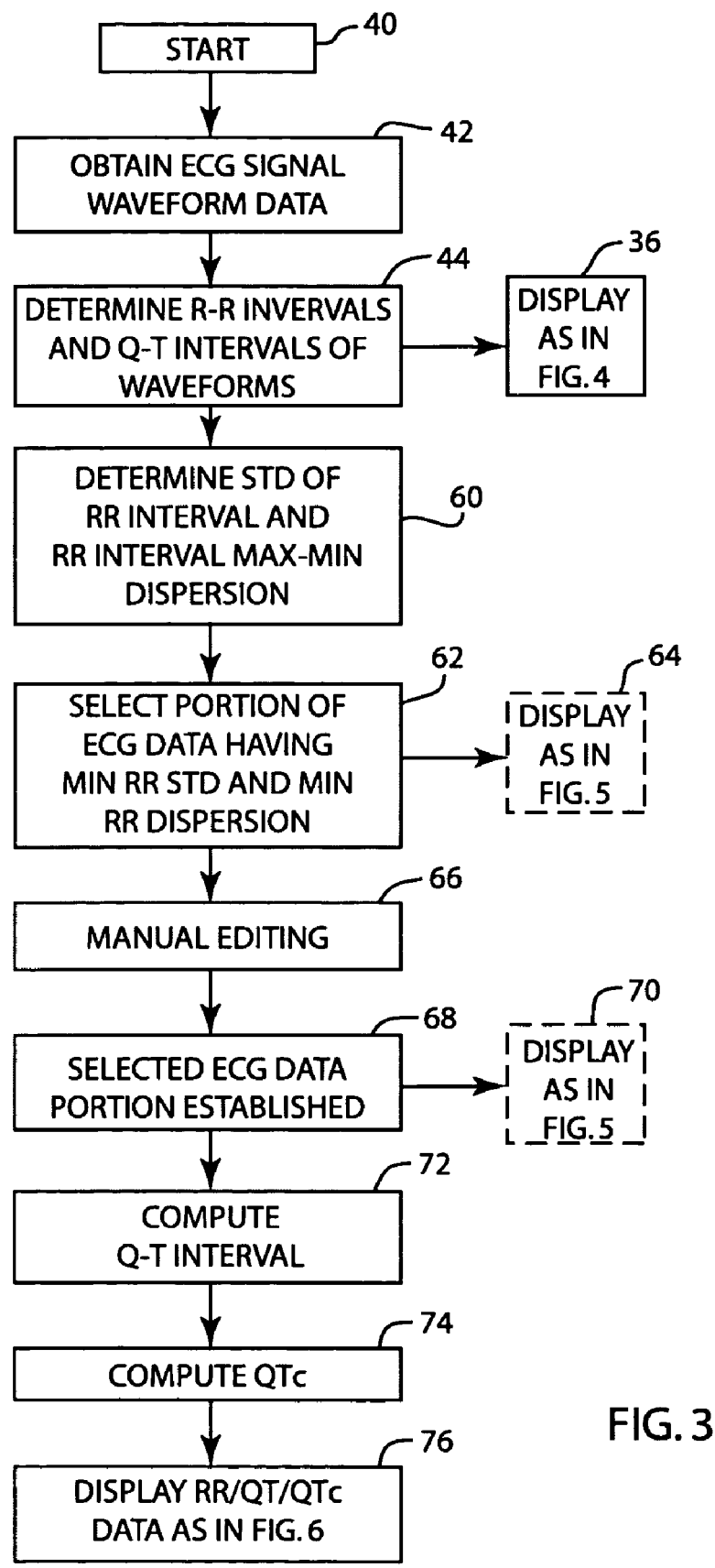
FIG. 3 is a flow chart showing the steps of a method of the present invention.
Figure 4A:
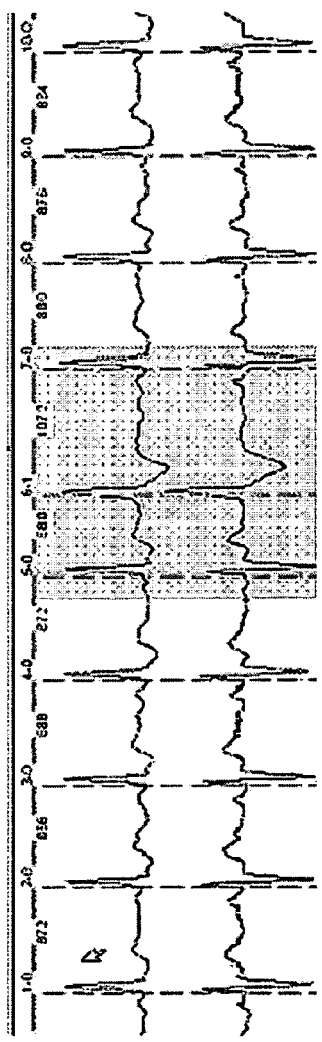
FIGS. 4A, 4B, and 4C show data displays employed in the present invention.

An embodiment of the method of the present invention is shown in the flow chart of FIG. 3. Following the start of the method at step 40, ECG signal data in the form of a series of sequential waveforms is obtained, either as it is received from subject 12, or more typically from the data stored in memory 18 of computer 20. This occurs at step 42. The data so obtained is shown in FIG. 4A containing two leads of ECG signal data for a typical sampling period of about 10 seconds. In FIG. 4A, the heart beats are sequentially numbered.

The data is then analyzed to select ECG signal data waveforms having a relatively stable heart rate. Preferably, this is done by analyzing the ECG signal data to determine the magnitudes of the intervals between the R peaks of successive ECG waveforms, i.e. the R-R interval. The QT interval present in each waveform is also obtained. This is done at step 44 shown in FIG. 3. The R-R interval between the R peak of a given waveform and that of the preceding waveform is matched to the QT interval of the given waveform. The ECG signal data may be displayed on screen 22 in step 46 and the R-R interval is shown in milliseconds in FIG. 4A.

Figure 4B:
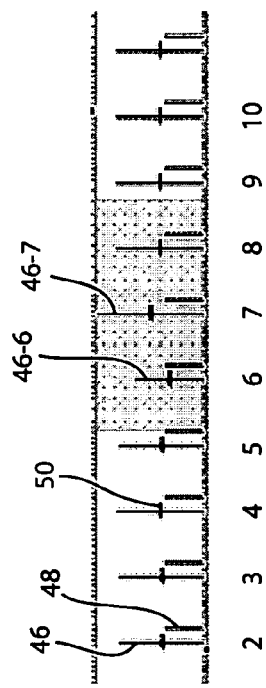

To provide a graphic indication of this data, it can be displayed on screen 22 in the manner shown in FIG. 4B in a time series relational map that shows the matched immediately previous R-R interval and Q-T interval data pairs as relational bars. The magnitude of the intervals is indicated by the height of the vertical lines. For the R-R interval, this is lines 46 and for the Q-T interval, it is lines 48. A uniformity in the height of the R-R interval lines 46 is a visual indication of the relative stability in the heart rate of the subject. The horizontal lines or ticks 50 on lines 46 indicate a certain fraction of the length of a line 46, for example, half or 50% of the R-R interval. This is helpfil to a clinician in visualizing the magnitudes of the R-R intervals and associated QT intervals. For example, a Q-T interval longer than half the previous R-R interval is a warning sign of a possible prolonged Q-T interval.

FIG. 4A shows the ECG waveform that produced the relational map or display of FIG. 4B. For beats 2 through 5, the extent of the R-R interval and the height of lines 46 is generally uniform, the R-R interval extending from 858 to 888 milliseconds. The R-R interval between beats 5 and 6 is shorter, 690 milliseconds, and the R-R interval between beats 6 and 7 is longer, 1072 milliseconds. This is reflected in the differing heights of lines 46-6 and 46-7, respectively, in FIG. 4B.

Figure 4C:
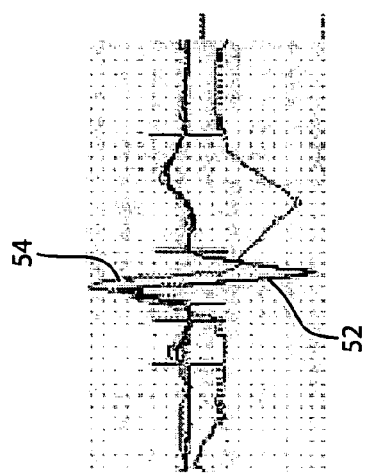

FIG. 4C shows another way of displaying the waveforms for presenting variations in their morphology and timing. In FIG. 4C, the ECG waveform data from successive heart beats is used to produce a median or average waveform that is displayed on screen 22 as the darker line 52. The waveform 54 for each heart beat is superimposed on the median waveform 52 so that atypical waveforms, and hence heart beats are readily apparent.

In an embodiment of the method of the present invention, the selection of the ECG signal data waveforms used to determine the QT interval and the QTc employs the standard deviation of the R-R interval, and also the dispersion of the maximum R-R interval to the minimum R-R interval.

The standard deviation is a measure of how closely data is clustered around a central or average value. The simplest measure of dispersion is the range, i.e. the difference between the maximum R-R interval and the minimum R-R interval found in a portion of ECG signal data. Other expressions of dispersion are available.

In an embodiment of the present invention, the ECG signal data waveforms selected are those having a minimum standard deviation STD of the R-R interval and a minimum dispersion of the R-R interval. The minimum standard deviation means that the R-R interval magnitudes of the selected portion of signal data are closely clustered around a central value. The minimum dispersion means that the difference between the maximum and minimum values is small. In the example of FIG. 4, the selected waveforms would be a portion including heart beat waveforms 1 through 5.

Figure 5A:
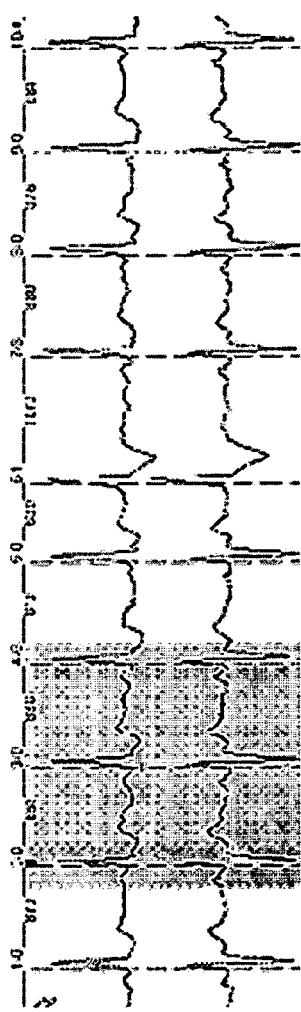
FIGS. 5A, 5B, and 5C are similar to FIG. 4 and graphically show properties of a portion of the ECG signal data selected for use in the present invention to determine properties of the Q-T interval.

The determination of the standard deviation of the R-R interval and the R-R interval maximum-minimum dispersion and the selection of a portion of the ECG signal data having minimum R-R interval standard deviation and minimum R-R interval dispersion is carried out at steps 60 and 62 of the method. The selected portion of the data is displayed in FIGS. 5A, B and C more particularly as heartbeat waveforms 2-4, as indicated in step 64 of FIG. 3

Figure 5B:
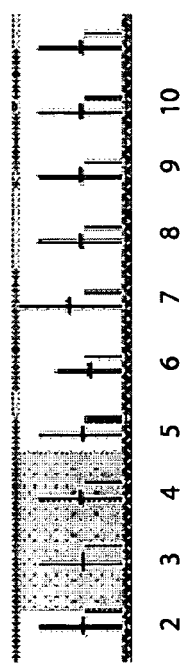
Figure 5C:
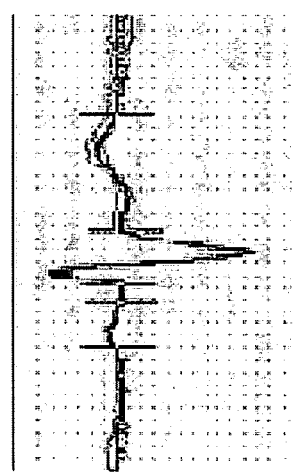

In step 66, a clinician may manually edit the ECG signal data with respect to the ECG signal data waveforms to be used, using either or both of displays in the form of FIG. 4 or FIG. 5. The portion of ECG data to be used in the further steps of the method, as selected by the criteria of steps 60 and 62 and/or manually in step 66, is established at step 68 and displayed in step 70.

In step 72, the QT interval is computed for each selected waveform of the signal data or is obtained from the previous determination made in step 44.

In step 74, the QTc indicative of the effect of the heart rate on the QT interval is determined for the waveforms of the selected portion of the ECG signal data. A number of formulae are commonly used for this purpose. These include the Bazett formula ($QTc=QT/RR^{1/2}$), the Friderica formula ($QTcF=QT/RR^{1/3}$), and the linear regression equitation ($QTcL=QT+0.154\times[1-RR]$). The linear regression equitation formula is often termed the Framingham formula with reference to the Framingham, Mass., longitudinal heart study. The computation of the QTc is carried out for each heart beat waveform in the selected portion of ECG signal data.

Figure 6:
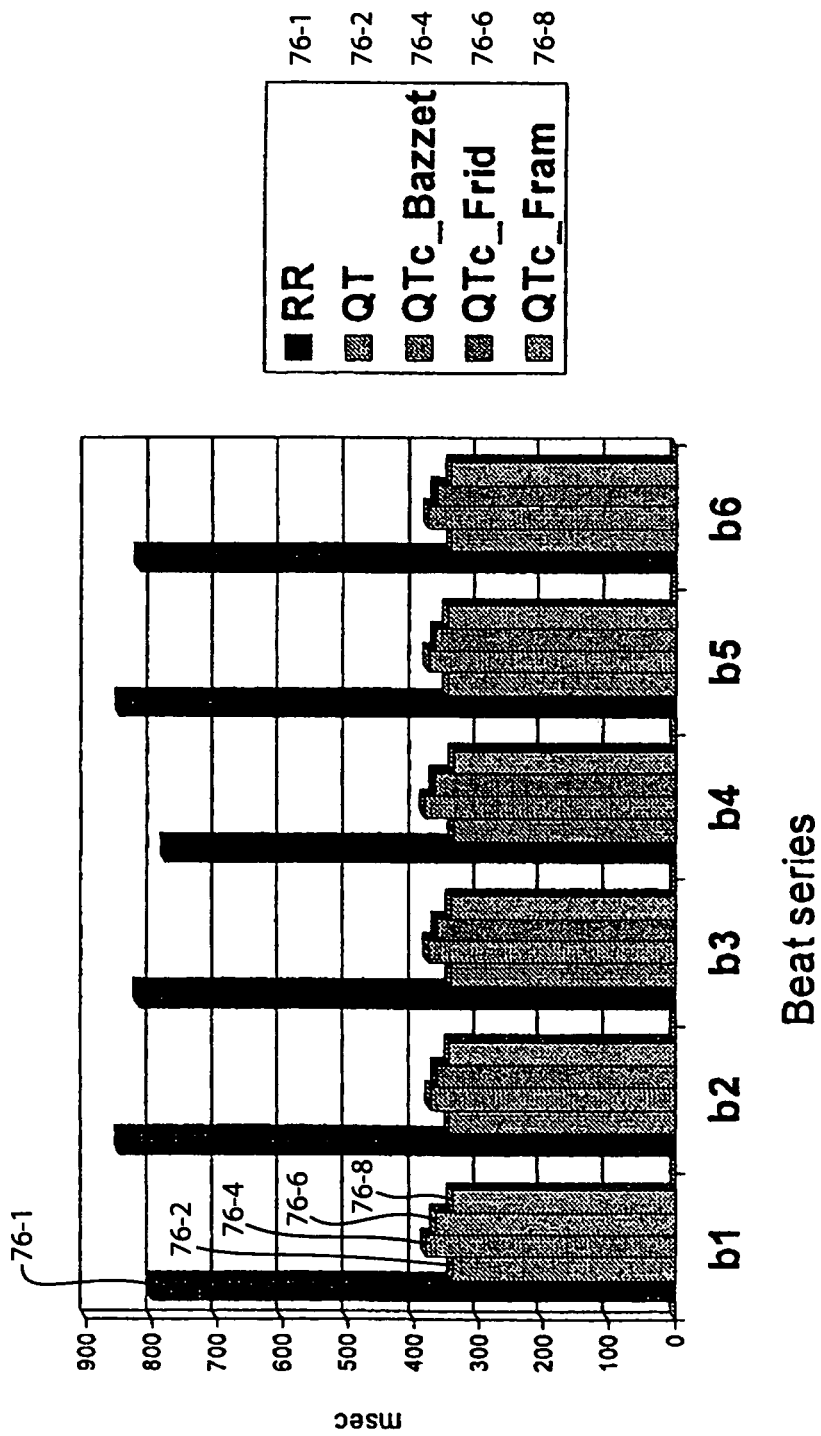
FIG. 6 shows a further display of the present invention.

In step 76, data is displayed in the manner shown in FIG. 6 for the selected heart beat waveforms of the ECG signal data. As shown in FIG. 6, the data is preferably graphically displayed as multiple vertical bars with time in milliseconds on the ordinate. The data displayed includes the R-R interval 76-1, the QT interval 76-2, and the QT correction determined by various formulae, 76-4, 76-6, and 76-8. The display of FIG. 6, allows RR/QT/QTc trending in order to monitor real-time dynamic change of QTc values with a view to identifying changes in QT interval properties indicative of potentially adverse conditions for subject 12.

In another aspect of the present invention, graphical displays of the type shown in FIGS. 4 and 5 may be extended to more general time series relational map displays to graphically show and compare two or more aspects of the ECG waveform signal data on a time series basis for use by a clinician. For example, the graphical showing may be that of a cardiac depolarization related feature along with a cardiac repolarization feature. Or, the displayed aspects may both relate to depolarization phenomena, but one may be a ventricular depolarization related feature and the other an atrial depolarization related feature.

Figure 7:
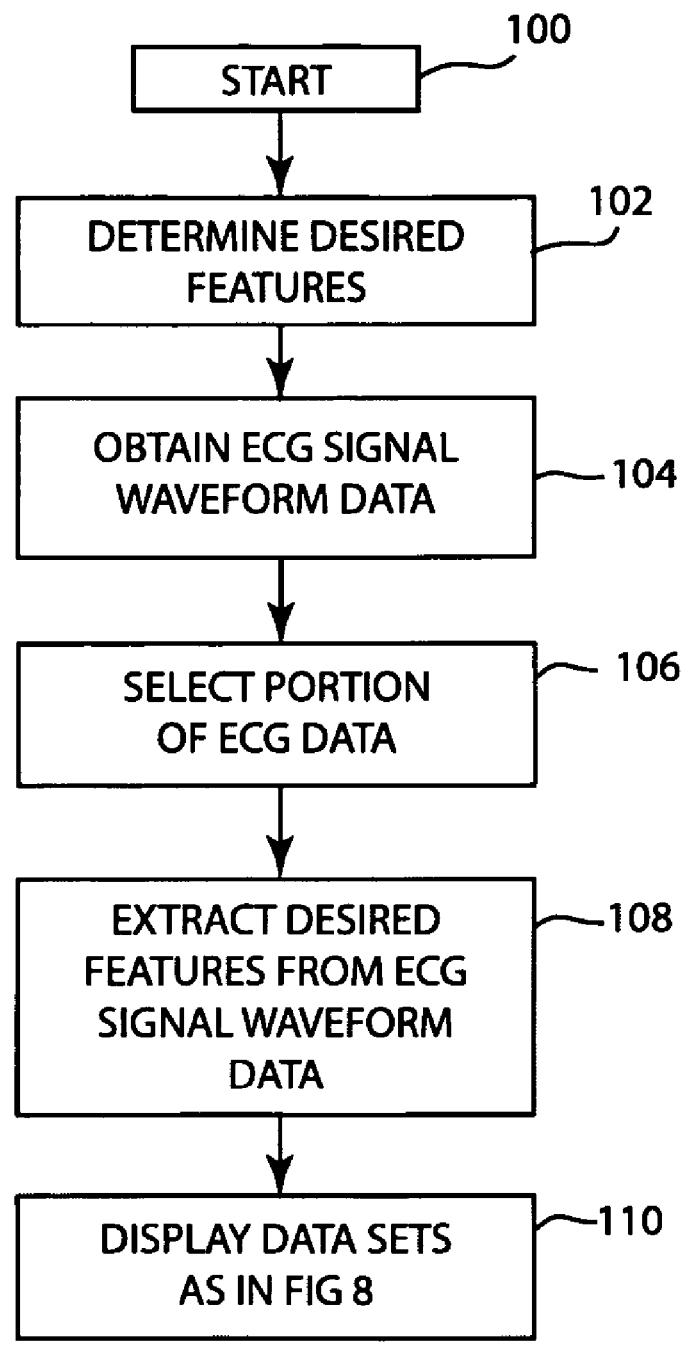
FIG. 7 is a flow chart showing a further embodiment of the method of the present invention.
Figures 8A, 8B, 8C:
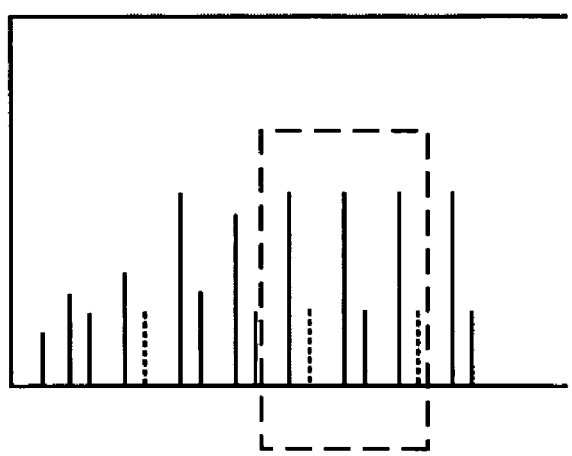
FIGS. 8A and 8B are tables showing electrocardiographic features that may be used in the method shown in FIG. 7.
FIG. 8C is a graphical showing similar to FIGS. 4B and 5B of a display of the present invention.

To carry out this aspect of the present invention, following a start at step 100 of FIG. 7, the desired features to be displayed are determined at step 102. For example, FIG. 8A shows typical cardiac depolarization related features and repolarization features that may be paired to produce a display, such as that shown in FIG. 8C. FIG. 8B shows a similar tabulation of ventricular depolarization related features and atrial depolarization features that may be paired. The features relating to, for example, the QRS wave axis or the P wave axis, are determined by the well known principles of vectorial analysis of electrocardiograms.

ECG signal waveform data is obtained in step 104. It will be appreciated that the sequence of steps 104 and 102 may be reversed, if desired.

If desired for the features being analyzed, a desired portion or waveforms of the ECG signal data may be selected in step 106. The selection may be carried out in the manner described above or in some other appropriate manner.

Thereafter, the desired features, such as a selected one of the depolarization related features and a selected one of the repolarization features shown in FIGS. 8A are extracted from the ECG signal waveform data at step 108. Thereafter, the data is displayed in the manner shown in FIG. 8C in step 110.

The result of the display of data in the manner shown in FIG. 8C is a beat-by-beat relational map for an ECG feature time series analysis. The relational map can be used in the same manner as described above in connection with the analysis of the R-R interval and the Q-T interval described using FIGS. 3 through 5.

Various alternatives and embodiments are contemplated as being within the scope of the following claims particularly pointing out and distinctly claiming the subject matter regarded as the invention.

What is claimed is:

1. A method for analyzing the characteristics of electrocardiographic (ECG) signal data, the method comprising the steps of:
    obtaining ECG signal data comprising a plurality of waveforms, each waveform comprising a depolarization feature and a repolarization feature;
    extracting, with a processor, the depolarization feature from each of the plurality of waveforms;
    selecting, with the processor, a set of stable waveforms from the plurality of waveforms based upon a statistical property of the extracted depolarization features;
    extracting, with the processor, the repolarization feature from each of the waveforms of the set of stable waveforms;
    computing, with the processor, an indication of Torsade de Pointes (TdP) from the extracted repolarization features, and
    presenting the indication of TdP on a graphical display.

2. The method of claim 1, wherein the repolarization feature is a Q-T interval.

3. The method of claim 2, wherein the depolarization feature is an R-R interval.

4. The method of claim 1, further comprising calculating, with the processor, the statistical property of the extracted depolarization features.

5. The method of claim 4 wherein the statistical property is a standard deviation of the depolarization features.

6. The method of claim 5 wherein the step of selecting a set of stable waveforms from the plurality of waveforms further comprises selecting waveforms wherein the depolarization feature of the waveform is within a predetermined standard deviation value threshold.

7. The method of claim 4, wherein the set of stable waveforms comprises a set of consecutive waveforms from the plurality of waveforms.

8. The method of claim 4, wherein the statistical property is a dispersion of the extracted depolarization features.

9. The method of claim 1, further comprising:
    presenting, on the graphical display, a plurality of data sets, each data set comprising an extracted depolarization feature and an extracted repolarization feature from one of the waveforms of the set of stable waveforms.

10. The method of claim 9, further comprising presenting, on the graphical display, the statistical property of the extracted depolarization features.

11. The method of claim 9, wherein the plurality of data sets are presented on the graphical display in the form of relational bars, a length of the relational bars proportioned to a magnitude of the extracted depolarization feature and the extracted repolarization feature of each of the plurality of data sets.

12. The method of claim 11, further comprising presenting on the graphical display an indicator on a depolarization feature relational bar, the indicator being indicative of a predetermined fraction of an amount of elongation of the bar.

13. A method of analyzing the characteristics of electrocardiographic (ECG) signal data, the method comprising the steps of:
    obtaining ECG signal data comprising a plurality of waveforms, each waveform comprising a depolarization feature and a repolarization feature;
    extracting, with a processor, the depolarization feature from each of the plurality of waveforms;
    selecting, with the processor, a set of stable waveforms from the plurality of waveforms based upon a statistical property of the extracted depolarization features;
    extracting, with the processor, the repolarization feature from each of the waveforms of the set of stable waveforms;
    computing, with the processor, QT correction (QTc) from the extracted repolarization features, and
    presenting the QTc on a graphical display.

14. The method of claim 13 wherein the QTc is computed using a formula selected from a list of formulas comprising a Bazett formula, a Friderica formula, and a Framingham formula.

15. The method of claim 13, further comprising calculating, with the processor, the statistical property of the extracted depolarization features.

16. The method of claim 15, wherein the statistical property is a standard deviation of the depolarization features.

17. The method of claim 16, wherein the step of selecting a set of stable waveforms from the plurality of waveforms further comprises selecting waveforms wherein the depolarization feature of the waveform is within a predetermined standard deviation value threshold.

18. The method of claim 15, wherein the statistical property is a dispersion of the extracted depolarization features.

19. The method of claim 15, wherein the set of stable waveforms comprises a set of consecutive waveforms from the plurality of waveforms.

* * * * *

UNITED STATES PATENT AND TRADEMARK OFFICE
CERTIFICATE OF CORRECTION

PATENT NO.           : 7,813,792 B2                                            Page 1 of 1
APPLICATION NO.      : 11/405150
DATED                : October 12, 2010
INVENTOR(S)          : Xue et al.

It is certified that error appears in the above-identified patent and that said Letters Patent is hereby corrected as shown below:

In Column 3, Line 59, delete "helpfil" and insert -- helpful --, therefor.

In Column 4, Line 57, delete "Friderica" and insert -- Fridericia --, therefor.

In Column 6, Line 63, in Claim 14, delete "Friderica" and insert -- Fridericia --, therefor.

Signed and Sealed this
Eighth Day of March, 2011

David J. Kappos
*Director of the United States Patent and Trademark Office*